(12) United States Patent
Suh et al.

(10) Patent No.: US 10,495,615 B2
(45) Date of Patent: Dec. 3, 2019

(54) EVALUATION SYSTEMS OF BLOCK COPOLYMER PATTERNS

(71) Applicant: SAMSUNG ELECTRONICS CO., LTD., Suwon-si, Gyeonggi-do (KR)

(72) Inventors: Min-Soo Suh, Hwaseong-si (KR); Hyun-Young Park, Seoul (KR); Jung-Dae Park, Yongin-si (KR); Ki-Hyun Kim, Suwon-si (KR); Kwang-Shin Lim, Yongin-si (KR)

(73) Assignee: Samsung Electronics Co., Ltd., Suwon-Si, Gyeonggi-do (KR)

( * ) Notice: Subject to any disclaimer, the term of this patent is extended or adjusted under 35 U.S.C. 154(b) by 444 days.

(21) Appl. No.: 15/242,748

(22) Filed: Aug. 22, 2016

(65) Prior Publication Data

US 2017/0089871 A1 Mar. 30, 2017

(30) Foreign Application Priority Data

Sep. 25, 2015 (KR) .......................... 10-2015-0136001

(51) Int. Cl.
*G01N 30/88* (2006.01)
*C08F 297/02* (2006.01)
*G01N 5/04* (2006.01)
*G01N 30/74* (2006.01)
*C08L 53/00* (2006.01)
*G01N 33/44* (2006.01)
*G03F 7/00* (2006.01)

(52) U.S. Cl.
CPC .......... *G01N 30/88* (2013.01); *C08F 297/026* (2013.01); *C08L 53/00* (2013.01); *G01N 5/04* (2013.01); *G01N 30/74* (2013.01); *G01N 33/442* (2013.01); *G03F 7/0002* (2013.01); *B81C 2201/0149* (2013.01); *G01N 2030/885* (2013.01)

(58) Field of Classification Search
CPC ........ G03F 7/0002; C08L 53/00; C08L 25/06; G01N 33/442; G01N 30/74; G01N 2030/885; G01N 5/04; G01N 30/88; B81C 2201/0149; C08F 297/026
See application file for complete search history.

(56) References Cited

U.S. PATENT DOCUMENTS 5,587,082 A 12/1996 Teraoka et al.
7,507,337 B2 3/2009 Petro et al.
8,263,323 B2 9/2012 Yoon et al.
(Continued)

FOREIGN PATENT DOCUMENTS

JP 2010-256016 A 11/2010
JP 2014-015607 A 1/2014
(Continued)

*Primary Examiner* — Shogo Sasaki
(74) *Attorney, Agent, or Firm* — Lee & Morse, P.C.

(57) ABSTRACT

An evaluation system of block copolymer patterns includes a supplier, a plurality of analyzers, and a homopolymer interference remover. The supplier provides a sample including a block copolymer and a homopolymer. The analyzers measure a molecular weight of the block copolymer in the sample, measure a preliminary block ratio, the preliminary block ratio corresponding to a total ratio in the sample of each block in the block copolymer, and selectively measure a ratio of the homopolymer in the sample. The homopolymer interference remover subtracts the ratio of the homopolymer from the preliminary block ratio.

9 Claims, 10 Drawing Sheets

(56) References Cited

U.S. PATENT DOCUMENTS

| | | |
|---|---|---|
| 2010/0286351 A1 | 11/2010 | Yoshida et al. |
| 2014/0087293 A1 | 3/2014 | Kandanarachchi et al. |
| 2015/0034595 A1 | 2/2015 | Seshimo et al. |

FOREIGN PATENT DOCUMENTS

| | | |
|---|---|---|
| JP | 2014-115640 A | 6/2014 |
| JP | 2015-089894 A | 5/2015 |
| KR | 10-2014-0099937 A | 8/2014 |

# EVALUATION SYSTEMS OF BLOCK COPOLYMER PATTERNS

CROSS-REFERENCE TO RELATED APPLICATION

Korean Patent Application No. 10-2015-0136001, filed on Sep. 25, 2015, and entitled, "Evaluation Systems of Block Copolymer Patterns," is incorporated by reference herein in its entirety.

BACKGROUND

1. Field

One or more embodiments described herein relate to evaluation systems of block copolymer patterns.

2. Description of the Related Art

A variety of methods have been developed to form fine and minute patterns for semiconductor devices with increased integration and capacity. However, these methods have drawbacks. For example, a photo-lithography process uses an exposure device in an attempt to form fine and minute patterns. However, this process is unable to accurately produce patterns with specific critical limits because of resolution limits.

A double patterning method uses at least two different masks in an attempt to form fine and minute patterns. However, this method requires the performance of complicated steps and is excessively expensive to implement.

A direct self assembly (DSA) method uses a block copolymer to form fine and minute patterns. One type of DSA method requires fine control of self-aligned block copolymer patterns.

SUMMARY

In accordance with one or more embodiments, an evaluation system of block copolymer patterns includes a sample supplier to provide a sample including a block copolymer and a homopolymer; a molecular weight analyzer to measure a molecular weight of the block copolymer in the sample; a preliminary block ratio analyzer to measure a preliminary block ratio, the preliminary block ratio corresponding to a total ratio in the sample of each block in the block copolymer; a homopolymer analyzer to selectively measure a ratio of the homopolymer in the sample; and a homopolymer interference remover to subtract the ratio of the homopolymer from the preliminary block ratio.

The molecular weight analyzer may include a gel permeation chromatography (GPC) device, a mass spectrometry (MS) device, or a nuclear magnetic resonance (NMR) device. The preliminary block ratio analyzer may include gel permeation chromatography (GPC) device or a nuclear magnetic resonance (NMR) device. The molecular weight analyzer and the preliminary block ratio analyzer may be integrated into a same device. A GPC device may serve as the molecular weight analyzer and the preliminary block ratio analyzer.

The evaluation system may include at least two different detectors coupled to the GPC device. The detectors may include a refractive index detector (RID) and an ultraviolet detector (UVD). The homopolymer analyzer may include a high-performance liquid chromatography (HPLC) device.

The molecular weight analyzer and the preliminary block ratio analyzer may be integrated into one molecular weight/preliminary block ratio analyzer, and the homopolymer analyzer and the molecular weight/preliminary block ratio analyzer may be sequentially and serially connected. The homopolymer analyzer may include an HPLC device, and the molecular weight/preliminary block ratio analyzer may include a GPC device serially connected to the HPLC device.

The evaluation system may include a mixer between the homopolymer analyzer and the molecular weight/preliminary block ratio analyzer, wherein polymers are to be recollected in the mixer. The evaluation system may include a factor calculator to generate pattern determining factors of the block copolymer; and a block critical dimension (CD) determiner to estimate a block CD formed from the block copolymer.

The pattern determining factors may include the molecular weight of the block copolymer obtained from the molecular weight analyzer; the ratio of the homopolymer obtained from the homopolymer analyzer; and a ratio of each block in the block copolymer obtained from the homopolymer interference remover or the factor calculator.

The block CD may be calculated based on the pattern determining factors, and the homopolymer interference remover, the factor calculator, and the block CD determiner may be integrated into a same device.

In accordance with one or more other embodiments, an evaluation system of block copolymer patterns includes a sample supplier to provide a sample including a block copolymer and a homopolymer; a molecular weight analyzer to measure a molecular weight of the block copolymer in the sample; a preliminary block ratio analyzer to measure a preliminary block ratio, the preliminary block ratio corresponding to a total ratio in the sample of each block in the block copolymer; a homopolymer analyzer to selectively measure a ratio of the homopolymer in the sample; and a calculator to estimate determining factors and a dimension of patterns formed from the block copolymer, the calculator to process values measured from the molecular weight analyzer, the preliminary block ratio analyzer, and the homopolymer analyzer.

The block copolymer may include polystyrene-b-polymethylmethacrylate (PS-b-PMMA), and the homopolymer may include at least one of a PS homopolymer or a PMMA homopolymer. A total PMMA ratio and a total PS ratio in the sample may be measured by the preliminary block ratio analyzer.

A PMMA ratio and a PS ratio in the block copolymer may be obtained through the calculator by removing an interference of the ratio of the homopolymer from the total PMMA ratio and the total PS ratio in the sample.

In accordance with one or more other embodiments, an apparatus includes first logic to measure a molecular weight of a block copolymer in a sample; second logic to measure a first block ratio corresponding to a total ratio in the sample of each block in the block copolymer; third logic to selectively measure a ratio of a homopolymer in the sample; fourth logic to subtract the homopolymer ratio from the first block ratio to obtain a block copolymer ratio; and fifth logic to determine a critical dimension of pattern of a semiconductor device based on the block copolymer ratio. The apparatus may include a calculator to generate pattern determining factors of the block copolymer, wherein the fifth logic is to estimate the critical dimension based on the pattern determining factors. The pattern determining factors may include the homopolymer ratio; a ratio of each block in the block copolymer; and the molecular weight of the block copolymer.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
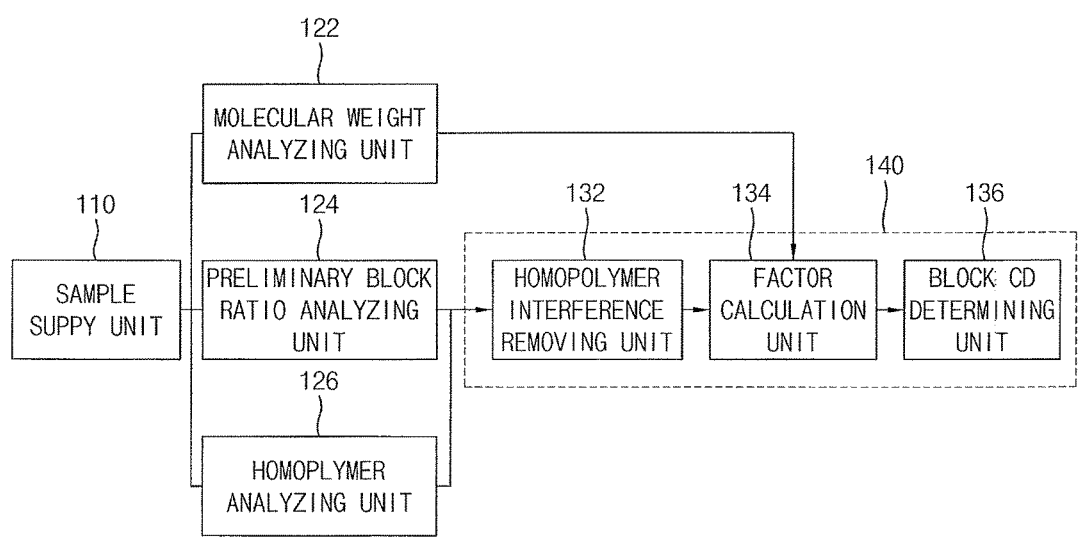
FIG. 1 illustrates an embodiment of an evaluation system.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art. The embodiments may be combined to form additional embodiments.

In the drawings, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third, fourth etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present application.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present application. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present application.

Unless otherwise defined, all terms (including technical and scientific terms) used herein have the same meaning as commonly understood by one of ordinary skill in the art to which this application belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 2:
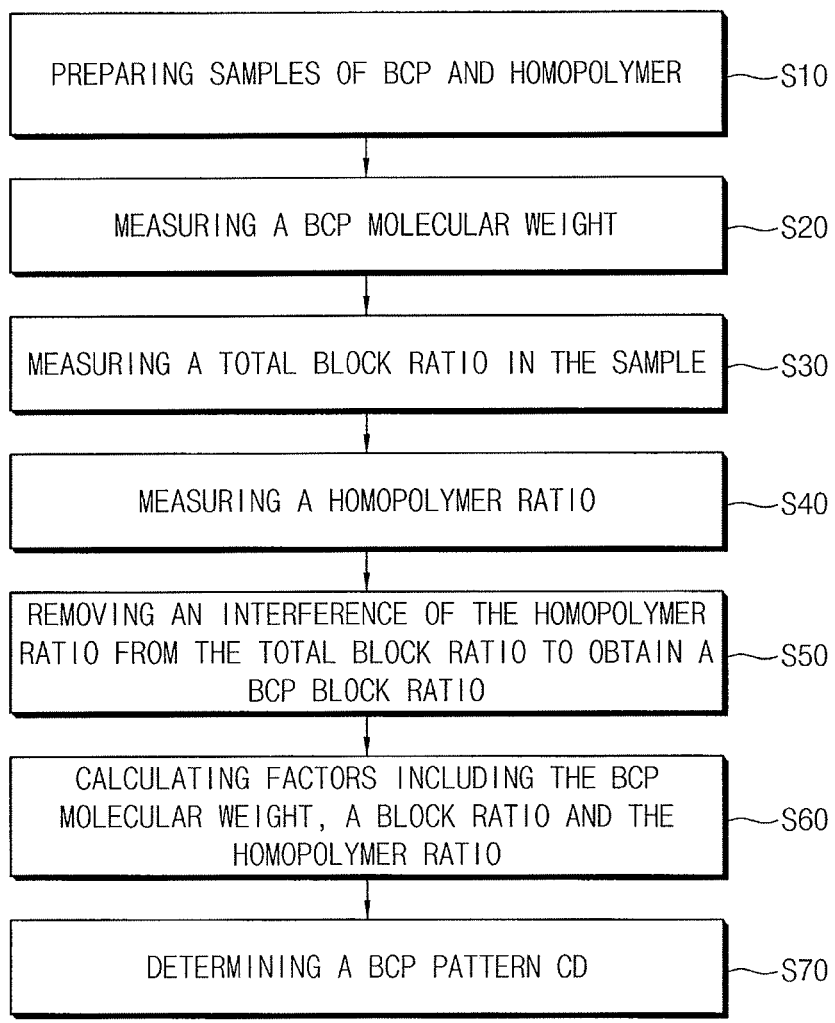
FIG. 2 illustrates an embodiment of a method for evaluating block copolymer patterns.

FIG. 1 illustrates an embodiment of an evaluation system 100 of block copolymer patterns. FIG. 2 illustrates an embodiment of a method for evaluating block copolymer patterns. (Operational numbers in FIG. 2 (e.g., S10 through S70) are not intended to limit an operational order or a process order, as one or more of the operations in FIG. 2 may be in a different order in another embodiment.)

Referring to FIGS. 1 and 2, a sample including a block copolymer (BCP) and a homopolymer may be prepared in operation S10. The sample may be stored, for example, in a sample supply unit 110 of the BCP pattern evaluation system 100 (hereinafter, referred to as an evaluation system). In example embodiments, the BCP may be utilized for implementing a direct self assembly (DSA) method. For example, the DSA method and the BCP may be utilized for forming a pattern of a semiconductor device which may have a critical dimension (CD) below about 20 nm. The CD may be in a different range in another embodiment.

Prediction of pattern type and pattern CD formed by the BCP may be performed for achieving a desired target pattern. The pattern type and pattern CD may be predicted or determined with a high reliability using the evaluation system 100.

In some embodiments, the pattern type and pattern CD may be predicted from one or more pattern determining factors, e.g., molecular weight of the BCP, block ratio in the BCP, and/or homopolymer ratio. The pattern type formed from the BCP may be determined, for example, among a spot type, a cylinder type, a gyro type, or a lamellar type based on the pattern determining factors. Further, the pattern CD may be predicted from an experimental equation which, for example, includes the pattern determining factors as variables thereof.

The BCP may be a copolymer of polymer units having different chemical properties. For example, the BCP may be synthesized by a cationic polymerization or an anionic polymerization of first and second polymer units. The first polymer unit may be more hydrophilic than the second polymer unit.

Examples of the first polymer unit include polymethylmethacrylate (PMMA), polydimethylsiloxane (PDMS), polyvinylpyrrolidone (PVP), polyethyleneoxide (PEO), polylactide (PLA), and polyimide (PI). The second polymer unit may include, for example, polystyrene (PS). Accordingly, the block copolymer may be represented as PS-b-PMMA, PS-b-PDMS, PS-b-PVP, PS-b-PEO, PS-b-PLA or PS-b-PI.

Hereinafter, detailed descriptions are provided based on an example that the first polymer unit and the second polymer unit are PMMA and PS, respectively, and the BCP is PS-b-PMMA. In this case, the BCP may include a first block containing PMMA and a second block containing PS.

The homopolymer may include polymers substantially the same as the first polymer unit and the second polymer unit. In example embodiments, the homopolymer may include a first homopolymer containing PMMA and a second homopolymer containing PS. In some embodiments, the sample may include one of the first homopolymer or the second homopolymer.

A quantitative analysis of the BCP and the homopolymer in the sample may be performed, for example, through operations S20 to S40. In example embodiments, the sample may be introduced from the sample supply unit 110 individually to a molecular weight analyzing unit 122, a preliminary block ratio analyzing unit 124, and a homopolymer analyzing unit 126 to perform the quantitative analysis.

In some embodiments, the sample may be commonly provided to the molecular weight analyzing unit 122, the preliminary block ratio analyzing unit 124, and the homopolymer analyzing unit 126 from one sample supply unit 110. In this case, the sample may be substantially simultaneously provided to the molecular weight analyzing unit 122, the preliminary block ratio analyzing unit 124, and the homopolymer analyzing unit 126.

In some embodiments, the sample supply unit 110 may be individually coupled to each of the molecular weight analyzing unit 122, the preliminary block ratio analyzing unit 124, and the homopolymer analyzing unit 126. The sample supply unit 110 may be integrated with each of the molecular weight analyzing unit 122 the preliminary block ratio analyzing unit 124, and the homopolymer analyzing unit 126.

In some embodiments, the molecular weight analyzing unit 122, the preliminary block ratio analyzing unit 124, and/or the homopolymer analyzing unit 126 may include a solvent supply unit for transporting the sample. The solvent supply unit may be coupled to a pump to inject a solvent into the molecular weight analyzing unit 122, the preliminary block ratio analyzing unit 124, and/or the homopolymer analyzing unit 126 to be mixed with the sample.

In some embodiments, the molecular weight analyzing unit 122, the preliminary block ratio analyzing unit 124, and/or the homopolymer analyzing unit 126 may include a detector such as, for example, an ultraviolet detector (UVD) and/or a refractive index detector (RID). The detector may generate measured results which, for example, may be plotted on a graph.

In operation S20, a molecular weight of the BCP may be measured by the molecular weight analyzing unit 122. The molecular weight analyzing unit 122 may include an analysis device for measuring the molecular weight of a polymer. For example, the molecular weight analyzing unit 122 may include, e.g., a gel permeation chromatography (GPC) device, a mass spectrometry (MS) device, a nuclear magnetic resonance (NMR) device, or the like. In example embodiments, the GPC device may be used as the molecular weight analyzing unit 122. Peaks of the BCP and the homopolymer may be generated in the molecular weight analyzing unit 122. The molecular weight of the BCP may be measured from a dominant peak of the peaks.

In operation S30, a preliminary ratio of the first block including the first polymer unit PMMA) and a preliminary ratio of the second block including the second polymer unit (e.g., PS) in the sample may be measured by the preliminary block ratio analyzing unit 124. The preliminary ratio may be measured in, e.g., a weight percentage (wt %).

The preliminary ratio may be a total block ratio in the sample containing the BCP and the homopolymer. For example, the preliminary ratio of the first block may be a total ratio of PMMA in the BCP and the homopolymer. The preliminary ratio of the second block may be a total ratio of PS in the BCP and the homopolymer.

The preliminary block ratio analyzing unit 124 may include an analysis device for performing selective detection based on a functional group. In some example embodiments, a GPC device or an NMR device may be used as the preliminary block ratio analyzing unit 124.

In operation S40, a homopolymer ratio may be obtained by the homopolymer analyzing unit 126. As described above, the homopolymer may include the first homopolymer containing the first polymer unit and/or the second homopolymer containing the second polymer unit. In example embodiments, a total homopolymer ratio in the sample may be measured by the homopolymer analyzing unit 126.

In example embodiments, the homopolymer analyzing unit 126 may include an analysis device for selectively detecting the BCP and the homopolymer. In some embodiments, a high-performance liquid chromatography (HPLC) device may be used as the homopolymer analyzing unit 126.

In operation S50, an interference of the homopolymer ratio achieved in operation S40 may be removed from the total block ratio (e.g., the preliminary ratio) measured in operation S30. Accordingly, a pure block ratio of the BCP may be achieved. For example, the interference of the homopolymer ratio may be removed from the total block ratio in a homopolymer interference removing unit 132.

As described above, the total block ratio may include the preliminary ratio of the first block, which may be a total PMMA ratio in the sample, and the preliminary ratio of the second block which may be a total PS ratio in the sample. The homopolymer ratio measured in the homopolymer analyzing unit 126 may be subtracted from the preliminary ratio of the first block and the preliminary ratio of the second block. Therefore, a first block ratio (e.g., a PMMA block ratio) and a second block ratio (e.g., a PS block ratio) which may be pure ratios in the BCP may be calculated. An equation for removing interference of the homopolymer ratio may be embedded in the homopolymer interference removing unit 132.

In operation S60, the pattern determining factors may be numerically obtained and stored in a factor calculation unit 134. In example embodiments, the pattern determining factors may include the BCP molecular weight measured by the molecular weight analyzing unit, the homopolymer ratio measured by the homopolymer analyzing unit 126, and the block ratio calculated by the homopolymer interference removing unit 132.

In operation S70, a BCP pattern CD may be predicted or determined using the pattern determining factors. The BCP pattern CD may be calculated from a block CD determining unit 136 utilizing the pattern determining factors calculated and stored in the factor calculation unit 134. In some embodiments, an experimental equation for predicting the BCP pattern CD may be embedded in the block CD determining unit 136. The pattern determining factors may be included in the experimental equation as variables thereof.

As illustrated in FIG. 1, a calculation unit 140 may include the homopolymer interference removing unit 132, the factor calculation unit 134, and the block CD determining unit 136. In one embodiment, the homopolymer interference removing unit 132, the factor calculation unit 134, and the block CD determining unit 136 may be integrated in the calculation unit 140. For example, calculations or operations of the homopolymer interference removing unit 132, the factor calculation unit 134, and the block CD determining unit 136 may be performed in one computer or processing device.

Figure 3:
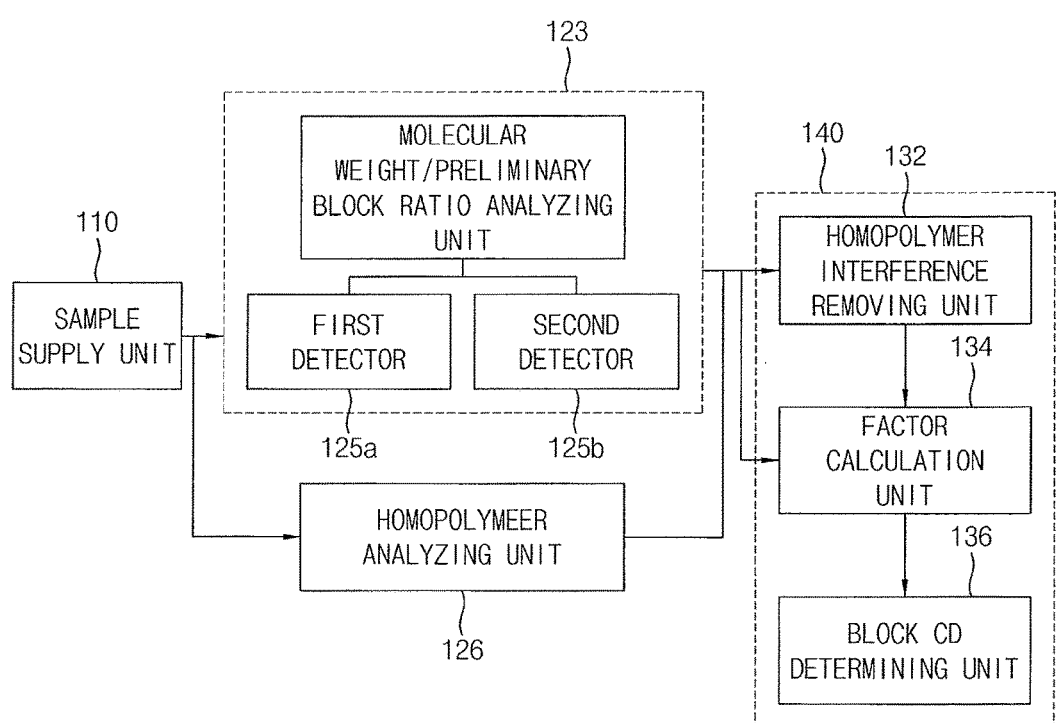
FIG. 3 illustrates another embodiment of an evaluation system.

FIG. 3 illustrates another embodiment of an evaluation system 100*a* of block copolymer patterns. Referring to FIG. 3, the molecular weight analyzing unit 122 and the preliminary block ratio analyzing unit 124 in the evaluation system 100*a* of FIG. 1 may be integrated into one device or one unit.

The evaluation system 100*a* may include a molecular weight/preliminary block ratio analyzing unit 123. In some embodiments, the molecular weight/preliminary block ratio analyzing unit 123 may include a GPC device. As described above, a BCP molecular weight may be measured by the GPC device.

The molecular weight/preliminary block ratio analyzing unit 123 may be coupled to different types of detectors, and a preliminary block ratio (e.g., a total block ratio in a sample) may be measured by the detectors.

For example, the detectors may include a first detector 125*a* and a second detector 125*b*. Measured values from the first and second detectors 125*a* and 125*b* may be interrelated with each other and adjusted to result in a preliminary ratio of a first block (e.g., a total ratio of PMMA) and a preliminary ratio of a second block (e.g., a total ratio of PS). In some embodiments, the first detector 125*a* may include an RID, and the second detector 125*b* may include a UVD. For example, the RID and the UVD may provide a signal intensity linearly proportional to a PS concentration. The RID may generate a signal representing a sum of PS and PMMA, and the UVD may generate a signal representing PS which may have an absorbance at a specific wavelength. Thus, the signals from the RID and the UVD may be interrelated to produce the total PMMA ratio and the total PS ratio in the sample.

Subsequently, as described with reference to FIGS. 1 and 2, a homopolymer ratio in the sample may be obtained by a homopolymer analyzing unit 126. The homopolymer ratio may be subtracted from the preliminary block ratio (e.g., the total PMMA ratio and the total PS ratio) in the homopolymer analyzing unit 126 so that pure block ratios in a BCP (e.g., a PMMA block ratio and a PS block ratio) may be calculated.

Data of pattern determining factors may be produced in a factor calculation unit 134 and a block CD determining unit 136, and a pattern CD may be predicted by an experimental equation.

In example embodiments, Equations (10) and (11) derived from the Experimental Example described below may be embedded in a homopolymer interference removing unit 132. Equations (12), (13), (16), and (17) derived from the Experimental Example may be embedded in the factor calculation unit 134. Equations (14) and (15) derived from the Experimental Example may be embedded in the block CD determining unit 136.

In some example embodiments, the homopolymer interference removing unit 132, the factor calculation unit 134, and the block CD determining unit 134 may be integrated in a calculation unit 140 (e.g., one computer or processing device). Accordingly, calculations for producing the pattern determining factors and predicting the pattern CD may be sequentially performed based on the equations in the calculation unit 140.

According to example embodiments as described with reference to FIGS. 1 to 3, at least two analysis devices may be combined. Numerical values obtained from the combination may be adjusted or revised by a calculation unit to predict the pattern type formed by the DSA method and determining factors of the pattern CD with improved accuracy.

For example, a BCP molecular weight may be measured by a GPC device. However, a block ratio in a BCP may not be obtained from the GPC device because separation of the BCP and a homopolymer may not be implemented in the GPC device. The separation of the BCP and the homopolymer also may not be implemented in the NMR device. Thus, the block ratio in the BCP may not be achieved. Direct analysis of a molecular weight may be performed in an MS device, and a component ratio may be predicted. However, the MS device may not provide separation of the homopolymer, and a molecular weight of the BCP having a large size may not be easily analyzed through the MS device. Separation of the homopolymer may be implemented by, for example, an HPLC device.

However, quantitative analysis of homopolymer content may not be implemented solely by the HPLC device, and the BCP molecular weight may not be obtained from the HPLC device. Thus, a pure block ratio in the BCP may not be achieved by removing interference of a homopolymer ratio in a sample using a single analysis device or a simple aggregation of the analysis devices.

According to example embodiments, a combination of the GPC device and the HPLC device may be utilized. The pure block ratio in the BCP may be obtained by a calculation in the homopolymer interference removing unit. The pure block ratio may be combined with the BCP molecular weight and the homopolymer ratio to predict or determine the pattern CD with high reliability.

Figure 4:
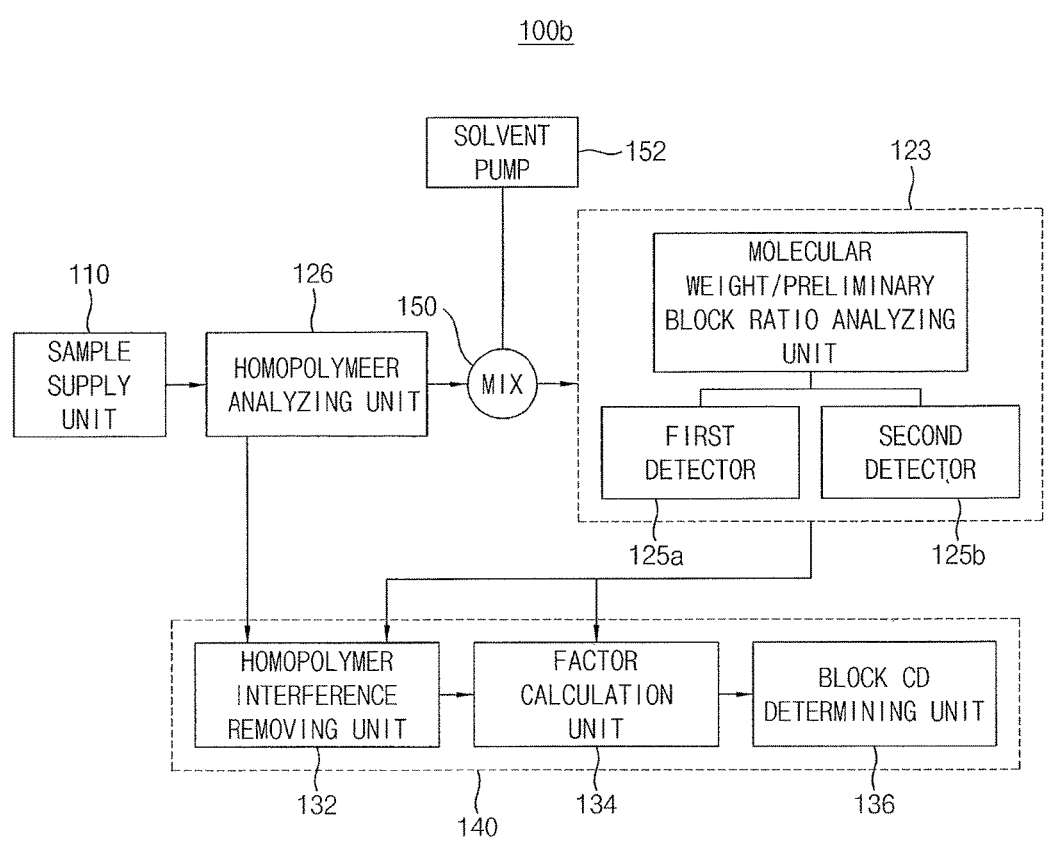
FIG. 4 illustrates another embodiment of an evaluation system.

FIG. 4 illustrates another embodiment of an evaluation system 100*b* of block copolymer patterns. Referring to FIG. 4, a homopolymer analyzing unit 126 and a molecular weight/preliminary block ratio analyzing unit 123 in the evaluation system 100b may be serially connected, and consecutive or sequential analyses may be performed.

The homopolymer analyzing unit 126 may include, for example, an HPLC device. The molecular weight/preliminary block ratio analyzing unit 123 may include a GPC device. In example embodiments, a sample including a BCP and a homopolymer may be introduced in the homopolymer analyzing unit 126, and a homopolymer ratio may be produced. The sample treated in the homopolymer analyzing unit 126 may be mixed again with a solvent by a mixing unit 150. For example, the mixing unit 150 may be coupled to a solvent pump 152, and recollected polymers and the solvent may be mixed in the mixing unit 150 to be introduced into the molecular weight/preliminary block ratio analyzing unit 123.

As described with reference to FIG. 3, a BCP molecular weight may be measured in the molecular weight/preliminary block ratio analyzing unit 123. A preliminary block ratio (e.g., a total ratio of PMMA and a total ration of PS) may be calculated based on signal values from first and second detectors 125a and 125b.

Subsequently, as also described with reference to FIGS. 1 and 2 or FIG. 3, pattern determining factors (e.g., the BCP molecular weight, a block ratio, and the homopolymer ratio) may be calculated by a homopolymer interference removing unit 132 and a factor calculation unit 134. A pattern CD may be predicted or determined by a block CD determining unit 136. As described above, the homopolymer interference removing unit 132, the factor calculation unit 134 and the block CD determining unit 136 may be integrated into a calculation unit 140 (e.g., one computer or processing device).

According to example embodiments as described above, the homopolymer analyzing unit 126 (e.g., the HPLC device) and the molecular weight/preliminary block ratio analyzing unit 123 (e.g., the GPC device) may be serially connected to perform an analysis substantially similar to that in a two-dimensional liquid chromatography (2D-LC). Thus, the resolution of polymer separation may be improved and accuracy of producing the pattern determining factors may be also improved.

The mixing unit 150 may be interposed between the homopolymer analyzing unit 126 and the molecular weight/preliminary block ratio analyzing unit 123 so that sequential analysis may be implemented. Thus, excessive analyzing time for performing a concurrent analysis in the 2D-LC may be avoided.

FIGS. 5 to 14 illustrate an embodiment of a method for forming patterns. FIGS. 5 to 10 and FIGS. 12 to 14 are cross-sectional views illustrating various stages of the method, and FIGS. 11A and 11B are top plan views illustrating various stages of the method. FIGS. 5 to 14 illustrate a method for forming patterns, for example, through a DSA method using a block copolymer.

Figure 5:
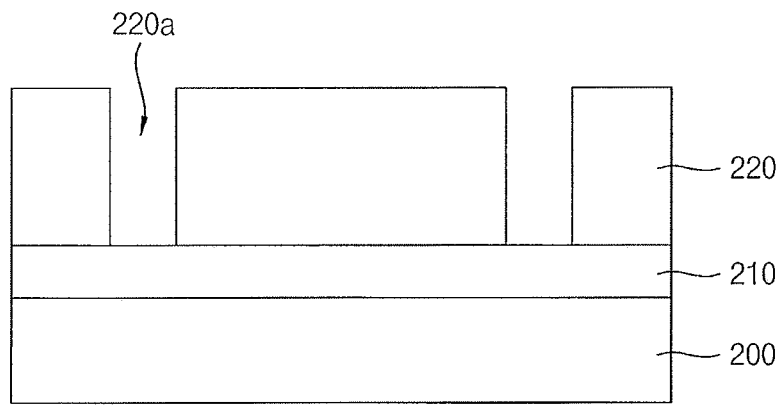
FIGS. 5 to 14 illustrate different stages of an embodiment of a method for forming patterns.

Referring to FIG. 5, an intermediate layer 210 and a sacrificial layer 220 may be sequentially formed on a substrate 200. The substrate 200 may include silicon, germanium, silicon-germanium or a group III-V compound such as GaP. GaAs, GaSb, etc. In some embodiments, the substrate 200 may be a silicon-on-insulator (SOI) substrate or a germanium-on-insulator (GOI) substrate.

In some embodiments, an object layer may be formed on the substrate 100. The object layer may be partially etched to be converted into a pattern including a plurality of openings or contact holes. In some embodiments, the object layer may be formed of a silicon oxide-based material such as plasma enhanced oxide (PEOX), tetraethyl orthosilicate (TEOS) or flowable oxide (FOX). In some embodiments, the object layer may be formed of a conductive material such as doped polysilicon, a metal, a metal nitride and/or a metal silicide.

The intermediate layer 210 may be formed of a material having an etching selectivity with respect to the object layer. In some embodiments, the intermediate layer 210 may be formed, for example, of silicon nitride, silicon oxynitride, silicon carbonitride and/or silicon carbide. The intermediate layer 210 may serve as an etch-stop layer or an etching mask layer for the object layer. The intermediate layer 210 may be formed as a multi-layered structure. The intermediate layer 210 may also include an anti-reflective layer.

The sacrificial layer 220 may be formed of a material having an etching selectivity with respect to the intermediate layer 210 and a guiding layer 230 (see, e.g., FIG. 7) formed by a subsequent process. In some embodiments, the sacrificial layer 220 may be formed of a silicon-based or carbon-based spin-on hardmask (SOH) material or a photoresist material.

The sacrificial layer 220 may include a plurality of guiding openings 220a therein. A top surface of the intermediated layer 210 may be exposed through the guiding opening 220a. For example, the guiding opening 220a may be formed by exposure and developing processes with respect to the sacrificial layer 220.

In some embodiments, the guiding opening 220a may have a trench shape extending linearly. In some embodiments, the guiding opening 220a may have a hole shape. In this case, a plurality of the guiding openings 220a may be formed in a honeycomb arrangement.

The object layer, the intermediate layer 210 and the sacrificial layer 220 may be formed, e.g., by a physical vapor deposition (PVD) process, a chemical vapor deposition (CVD) process, an atomic layer deposition (ALD) process, a sputtering process, a spin coating process, etc.

Figure 6:
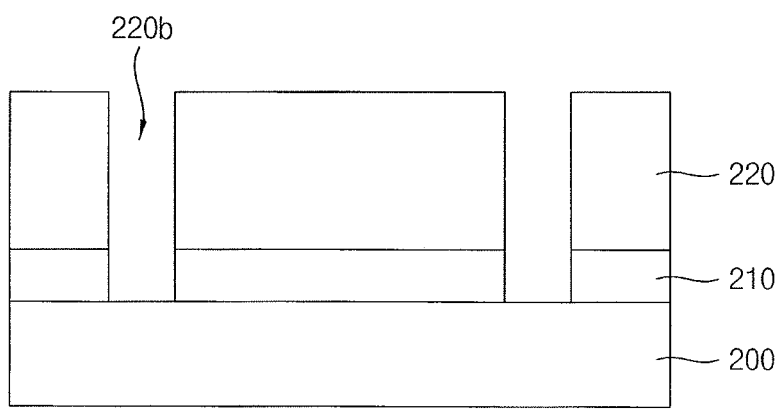

Referring to FIG. 6, the intermediate layer 210 may be partially etched through the guiding opening 220a in the sacrificial layer 220. Accordingly, an extended guiding opening 220b may be formed from the guiding opening 220a.

Figure 7:
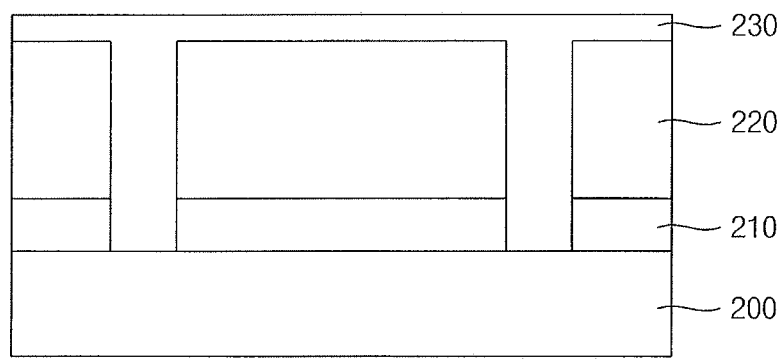

Referring to FIG. 7, the guiding layer 230 filling the extended guiding openings 220b may be formed on the sacrificial layer 220. In some embodiments, the guiding layer 230 may be formed of an oxide-based material such as an atomic layer deposition (ALD) oxide, a middle temperature oxide (MTO) or a high temperature oxide (HTO).

Figure 8:
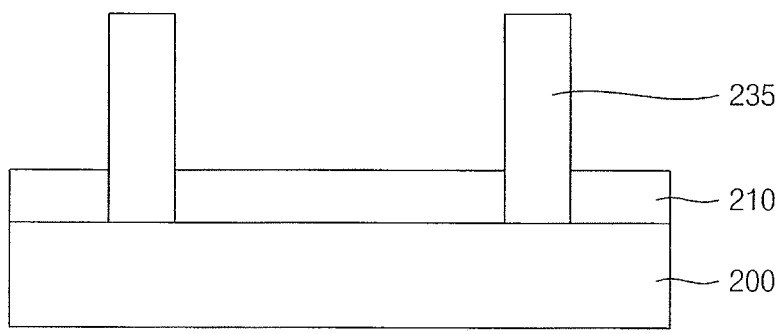

Referring to FIG. 8, a guiding pattern 235 may be formed from the guiding layer 230, and the sacrificial layer 220 may be removed. In example embodiments, an upper portion of the guiding layer 230 may be planarized by a chemical mechanical polish (CMP) process until a top surface of the sacrificial layer 220 may be exposed. Accordingly, the guiding layer 230 may be separated per each extended guiding opening 220b to form the guiding pattern 235.

The sacrificial layer 220 may be removed, for example, by an ashing process and/or a strip process. The guiding pattern 235 may be partially buried in the intermediate layer 210 and may protrude from a top surface of intermediate layer 210. In some embodiments, if the guiding opening 220a has the trench shape, the guiding pattern 235 may have a fence shape extending linearly. In some embodiments, if the guiding opening 220a may have a hole shape, the guiding pattern 235 may have a pillar shape or a cylindrical shape.

Figure 9:
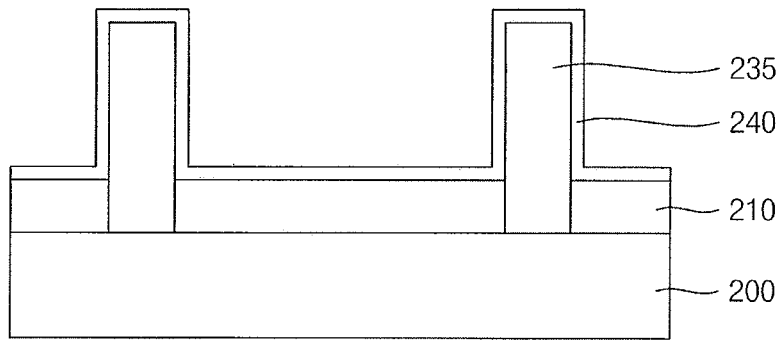

Referring to FIG. 9, a brush layer 240 may be formed along the top surface of the intermediate layer 210 and surfaces of the guiding patterns 235. In some embodiments, the brush layer 240 may be formed using a random copolymer, e.g., PS-r-PMMA. In this case, the brush layer 240 may serve substantially as a neutral layer.

In some embodiments, the brush layer 240 may serve as a layer for a hydrophilic surface treatment. In this case, the brush layer 240 may be formed using a hydrophobic polymer that may have a surface-bond moiety such as a hydroxyl group at a terminal portion thereof. For example, the brush layer 240 may be formed using PS—OH. The brush layer 240 may be formed, for example, using a composition that may include the random copolymer or the hydrophobic polymer by a spin coating process.

Figure 10:
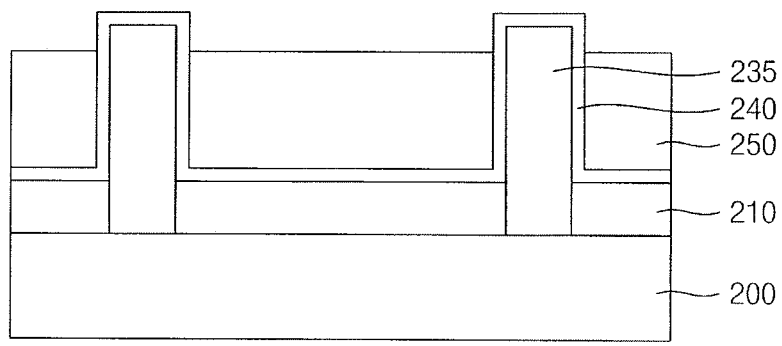

Referring to FIG. 10, a self-aligned layer 250 at least partially filling spaces between the guiding patterns 235 neighboring each other may be formed on the brush layer 240. The self-aligned layer 250 may be formed, for example, using a composition that may include a BCP such as PS-b-PMMA and a homopolymer by a spin coating process. In example embodiments, a composition capable of being self-aligned with proper pattern type (e.g., a self-aligned block type) and pattern CD (e.g., a self-aligned block CD) may be selected in consideration of a target pattern CD formed by the DSA method.

The evaluation system of BCP patterns described with reference to FIGS. 1 to 4 may be utilized to estimate the pattern type and the pattern CD formed from the composition. Thus, a proper composition comparable to the target pattern may be selected. As described above, pattern determining factors including a BCP molecular weight, a block ratio, and a homopolymer ratio may be calculated or produced by the evaluation system in accordance with example embodiments. The pattern CD may be predicted based on the pattern determining factors. Further, the pattern type may be predicted based on, e.g., the block ratio.

Figure 11A:
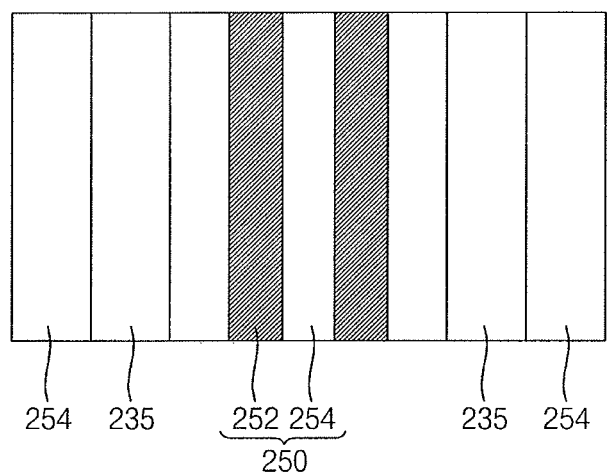
Figure 11B:
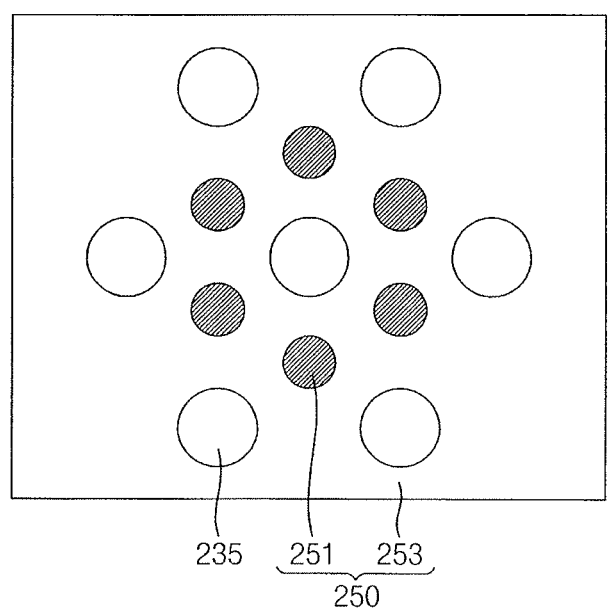

Referring to FIGS. 11A and 11B, the self-aligned layer 250 may be thermally treated, e.g., by an annealing process, to induce a phase-separation of the self-aligned layer 250. For convenience of descriptions, illustration of the brush layer 240 is omitted in FIGS. 11A and 11B.

A first polymer unit (e.g., PMMA) and a second polymer unit (e.g., PS) of the BCP in the self-aligned layer 250 may be separated from each other due to chemical and/or physical differences caused by the guiding pattern 235 and the brush layer 240 to be self-aligned or self-assembled.

The first polymer unit may be assembled to be spaced apart from the guiding pattern 235 by the brush layer 240 to form first blocks 251 and 252 (e.g., PMMA blocks). The second polymer unit may have an affinity to the brush layer 240 and may be assembled to form second blocks 253 and 254 (e.g., PS blocks) that surround sidewalls of the guiding patterns 235 and the first blocks 251 and 252.

As illustrated in FIG. 11A, if the guiding pattern 235 has a fence shape, the first block 252 and the second block 254 may be self-aligned or self-assembled in linear patterns. In this case, a composition including a lamellar type BCP may be selected utilizing the block ratio obtained by the evaluation system. For example, the lamellar type BCP may include a BCP, a ratio of the PMMA block with respect the PS block, for example, in the range from about 4:6 to about 6:4 (e.g., Examples 8 to 11 of Experimental Example described below).

As illustrated in FIG. 11B, if the guiding pattern 235 has a pillar shape or cylindrical shape, the first block 251 and the second block 253 may also be self-aligned or self-assembled in a pillar shape or cylindrical shape. For example, the first blocks 251 may be aligned in a polygonal arrangement such as a hexagonal arrangement to be radially expanded. In this case, a composition including a cylinder type BCP may be selected utilizing the block ratio obtained by the evaluation system. For example, the cylinder type BCP may include a BCP, a ratio of the PMMA block with respect the PS block greater than about 6:4 or less than about 4:6 (e.g., Examples 1 to 7 of the Experimental Example described below). A subsequent process may be described with reference to cross-sectional views of FIG. 11A.

Figure 12:
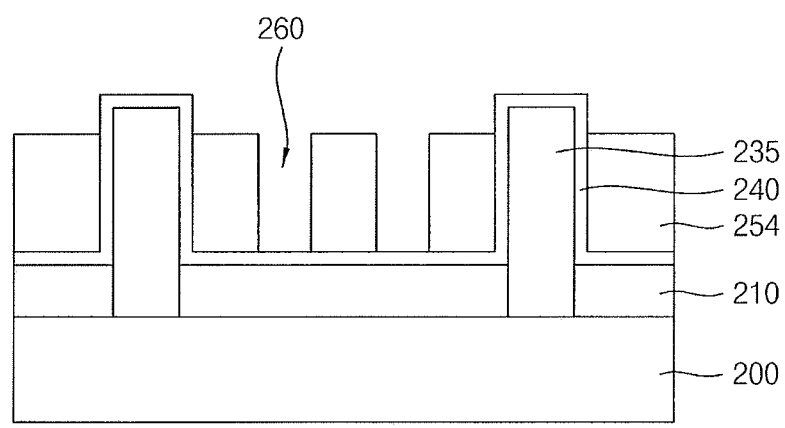

Referring to FIG. 12, the first blocks 252 may be selectively removed to form first openings 260. In example embodiments, the first blocks 251 may be removed, e.g., by a UV irradiation, a rinse process using a hydrophilic solution such as isopropyl alcohol, a reactive ion etching (RIE) process, an oxygen plasma etching process, etc.

Figure 13:
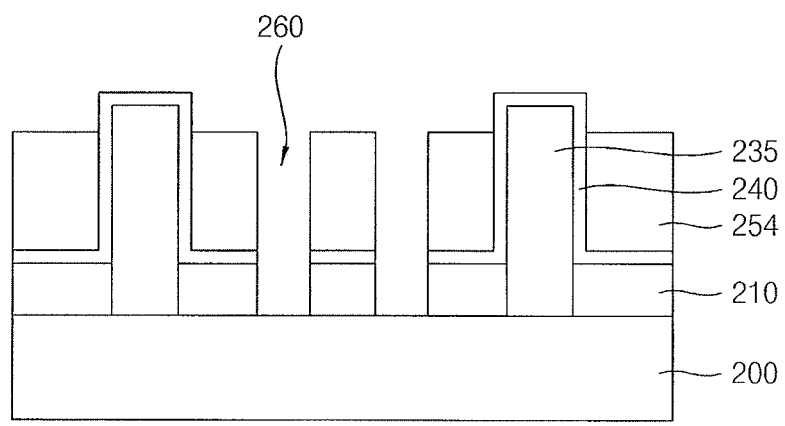

Referring to FIG. 13, the brush layer 240 and the intermediate layer 210 may be partially removed, e.g., by a dry etching process through the first openings 260. Accordingly, the first openings 260 may be extended in the intermediate layer 210. In some embodiments, a top surface of the object layer may be exposed through the extended first openings 260.

Figure 14:
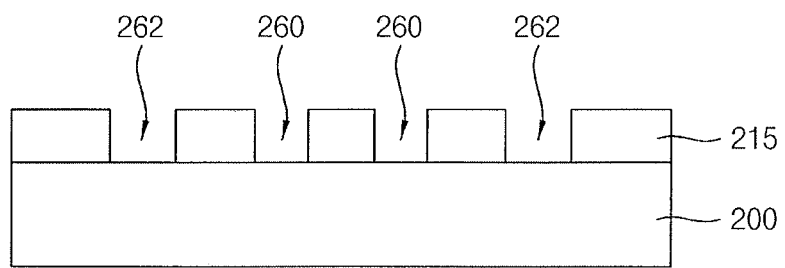

Referring to FIG. 14, an intermediate layer pattern 215 including the first openings 260 and second openings 262, formed by removing the guiding patterns 235 may be formed. For example, the remaining second blocks 254 and the brush layer 240 may be removed, for example, by an asking process and/or a strip process to expose the guiding patterns 235. The guiding patterns 235 may be removed, for example, using a fluoric acid solution or a buffer oxide etchant (BOE) solution. Accordingly, the second openings 262 may be defined in the intermediate layer 210 by spaces from which the guiding patterns 235 may be removed, and the intermediate layer pattern 215 including the first openings 260 and the second openings 262 therein may be formed.

The intermediate layer pattern 215 may serve as an etching mask with respect to the object layer. Thus, the object layer may be partially etched using the intermediate layer pattern 215, such that the desired target pattern may be transferred to the object layer.

According to example embodiments as described above, the pattern determining factors may be achieved using the evaluation system with a reduced error level. Also, the pattern type and the pattern CD may be predicted utilizing the pattern determining factors with an improved accuracy. Therefore, a proper BCP composition for forming the target pattern may be selected. Thus, reliability of a semiconductor device fabrication method may be improved.

Example embodiments of the evaluation system/method of BCP patterns will now be described with reference to an Experimental Example. However, the Experimental Example is only illustrative or exemplary of the embodiments herein.

Experimental Example

A sample including a BCP (PS-b-PMMA) and a PS homopolymer was prepared. A GPC device was employed as the molecular weight/preliminary block ratio analyzing unit 123. An HPLC device was employed as the homopolymer analyzing unit 126 in the evaluation system 100a of FIG. 3. RID and UVD were coupled to the GPC device as the first detector 125a and the second detector 125b, respectively.

1) RID/UVD Signal Corrections in the GPC Device

To observe sensitivity changes in the UVD and the RID depending on a concentration change of PS, signal intensities detected in the UVD (at a wavelength of 260 nm) and the RID were measured while changing a PS concentration from 0.003 wt % to 0.33 wt %. The signal intensities in the UVD and the RID were proportional to the PS concentration in a graph obtained by illustrating the signal intensity of each detector according to the PS concentration. Additionally, the ratio of the signal intensity in the RID with respect to the signal intensity in the UVD was about 75.07 substantially at all the PS concentrations, when comparing the sensitivities of the RID and the UVD with respect to the PS concentration. Accordingly, Equation (1) was derived as follows:

$$RID_{PS}=75.07\times UVD_{PS} \qquad (1)$$

where $RID_{PS}$ is an RID measured value with respect to PS, and $UVD_{PS}$ is a UVD measured value with respect to PS.

2) Analysis of BCP Molecular Weight and Preliminary Block Ratio: GPC Analysis

Two Polypore 300 mm columns were serially connected in the GPC device (manufactured by Waters). A tetrahydrofuran (THF) solvent was introduced therein at a flow rate of 0.8 mL/min to separate the BCP. The polymer separated from the column was detected by each of the UVD and RID. The molecular weight (Mn) of the BCP was measured based on a standard PS molecular weight. A total mixing ratio of PS and PMMA in the sample was calculated by properties of the UVD and the RID. Both PMMA and PS were detected by the RID, and PS was only detected by the UVD at a detection wavelength of 260 nm. The ratio of PMMA was calculated by subtracting a component amount measured in the UVD from a component amount measured in the RID.

Specifically, a total PS ratio in the sample was obtained by the UVD. A value calculated from the UVD was subtracted from an area value of an RID graph to obtain a PMMA area value detected in the RID, because a value from the RID corresponds to a sum of PS and PMMA.

Based on the above, Equation (5) was derived from Equations (2) to (4):

$$RID_{PS}=75.07\times GPC_{UVD} \qquad (2)$$

where $GPC_{UVD}$ is a total UVD measured value in the GPC, $$GPC_{RID}=RID_{PS}+RID_{PMMA} \qquad (3)$$

where $RID_{PMMA}$ is an RID measured value of PMMA and $GPC_{RID}$ is a total RID measured value in the GPC, and $$RID_{PMMA}=GPC_{RID}-RID_{PS} \qquad (4)$$

$$RID_{PMMA}=GPC_{RID}-75.07\times GPC_{UVD}. \qquad (5)$$

Subsequently, a preliminary block ratio of PS (a total PS ratio in the sample) and a preliminary block ratio of PMMA (a total ratio of PMMA in the sample) were calculated as weight percentage (wt %) as described below.

A material has an intrinsic value of a refractive index change ratio (dn/dc) per a unit concentration with respect to the RID. The value may be achieved, for example, by document sources or by experiment. The dn/dc values of PS and PMMA are 0.185 and 0.085, respectively.

The RID measured value correspond to "dn," and thus a weight percentage of PS and PMMA, were calculated by Equation (6).

$$\text{wt \%}_{PS} = RID_{PS}/(dn/dc)_{PS} \qquad (6)$$
$$= RID_{PS}/0.185$$
$$= 75.07\times GPC_{UVD}/0.185$$
$$= 405.8\times GPC_{UVD}$$

-continued
$$\text{wt \%}_{PMMA} = RID_{PMMA}/(dn/dc)_{PMMA} \qquad (7)$$
$$= RID_{PMMA}/0.085$$
$$= (GPC_{RID}-75.07\times GPC_{UVD})/0.085$$

3) Analysis of Homopolymers: HPLC Analysis

Extend-C18 (150 mm×4.6 mm, 100 Å, 5 μm) column was used. A combination of dichloromethane and acetonitrile was used as a solvent to perform an HPLC analysis. A ratio of dichloromethane and acetonitrile was changed from 45/55 to 75/25 at a flow rate of 5 ml/min. The HPLC analysis was performed at a UVD wavelength of 260 nm. The BCP and the homopolymer were separated from each other by the HPLC analysis, and a homopolymer ratio with respect to the BCP was achieved. PS of the BCP and the PS homopolymer were selectively detected by a combination of HPLC and UVD. A BCP ratio in the sample ($Ratio_{BCP}$) and the homopolymer ratio ($Ratio_{homo}$) were calculated by Equations (8) and (9).

$$Ratio_{BCP}=HPLC_{BCP}/(HPLC_{BCP}+HPLC_{homo}) \qquad (8)$$

where $HPLC_{BCP}$ is a BCP measured value in the HPLC and $HPLC_{homo}$ is a homopolymer measured value in the HPLC, and $$Ratio_{homo}=HPLC_{homo}/(HPLC_{BCP}+HPLC_{homo}). \qquad (9)$$

4) Removing a Homopolymer Interference

The PS ratio obtained by Equation (6) includes PS amounts of BCP and the homopolymer. Thus, a PS ratio in the BCP (wt $\%_{PS(BCP)}$) and a PS ratio in the homopolymer (wt $\%_{PS(homo)}$) were calculated based on Equation (10) and Equation (11), respectively, by combining Equations (8) and (9).

$$\text{wt \%}_{PS(BCP)} = 405.8\times GPC_{UVD}\times Ratio_{BCP} \qquad (10)$$
$$= 405.8\times GPC_{UVD}\times$$
$$(HPLC_{BCP}/(HPLC_{BCP}+HPLC_{homo}))$$

$$\text{wt \%}_{PS(homo)} = 405.8\times GPC_{UVD}\times Ratio_{homo} \qquad (11)$$
$$= 405.8\times GPC_{UVD}\times$$
$$(HPLC_{homo}/(HPLC_{BCP}+HPLC_{homo}))$$

5) Calculating Pattern Determining Factors

The BCP molecular weight (Mn) as one of pattern determining factors was obtained by the GPC, and a BCP block ratio and a homopolymer ratio were calculated by Equation (12) corresponding to the PS ratio in the homopolymer and the BCP block ratio (PS:PMMA).

$$Ratio_{PS(homo)} = \text{wt \%}_{PS(homo)}/(\text{wt \%}_{PS}+\text{wt \%}_{PMMA}) = \qquad (12)$$
$$405.8\times GPC_{UVD}\times(HPLC_{homo}/(HPLC_{BCP}+HPLC_{homo}))/$$
$$(405.8\times GPC_{UVD}+(GPC_{RID}-75.07\times GPC_{UVD})/0.085)$$

$$\text{Block Ratio }(PS:PMMA) = \text{wt \%}_{PS(BCP)}:\text{wt \%}_{PMMA} = \qquad (13)$$
$$(405.8\times GPC_{UVD}\times HPLC_{BCP}/(HPLC_{BCP}+HPLC_{homo})):$$
$$((GPC_{RID}-75.07\times GPC_{UVD})/0.085)$$

6) Predicting a Pattern CD

The pattern CD formed using the BCP may be predicted by Equation (14).

$$\text{Pattern CD (nm) estimation}=\{Mn/(Mw_{monomer1}\times Ratio_{monomer1}+Mw_{monomer2}\times Ratio_{monomer2})/3.2\}^{2/3}/(1-Ratio_{homo})^{0.83} \qquad (14)$$

In the Equation (14), monomer 1 and monomer 2 represent PS and PMMA, respectively. Thus, Equation (14) may be converted to Equation (15) according to the Experimental Example.

$$\text{Pattern CD (nm) estimation} = [Mn/(104.2 \times \text{Ratio}_{PS(BCP)} + 100.1 \times \text{Ratio}_{PMMA(BCP)})/3.2]^{2/3}/ \{(1-\text{wt }\%_{PS(homo)})/(\text{wt }\%_{PS}+\text{wt }\%_{PMMA})\}^{0.83} \quad (15)$$

The PS block ratio in the BCP ($\text{Ratio}_{PS(BCP)}$) and the PMMA block ratio in the BCP ($\text{Ratio}_{PMMA(BCP)}$) may be calculated by Equation (16) and Equation (17), respectively.

$$\text{Ratio}_{PS(BCP)} = \text{wt }\%_{PS(BCP)}/(\text{wt }\%_{PS}+\text{wt }\%_{PMMA}) \quad (16)$$

$$\text{Ratio}_{PMMA(BCP)} = \text{wt }\%_{PMMA}/(\text{wt }\%_{PS}+\text{wt }\%_{PMMA}) \quad (17)$$

The pattern CD values using a plurality of samples were calculated based on Equations (15), (16), and (17). The results are in Tables 1 and 2.

TABLE 1

Measured values from instrumental analyses

| | Mn | GPC (RID) | GPC (UVD) | HPLC (homo) |
|---|---|---|---|---|
| Example 1 | 52,888 | 838,195 | 8,933 | 0.07 |
| Example 2 | 58,879 | 792,825 | 8,377 | 0.19 |
| Example 3 | 136,614 | 286,176 | 3,252 | 2.2 |
| Example 4 | 132,248 | 313,853 | 3,964 | 18.4 |
| Example 5 | 92,209 | 305,294 | 3,500 | 9.3 |
| Example 6 | 64,218 | 172,192 | 2,045 | 6.6 |
| Example 7 | 70,186 | 295,991 | 3,196 | 0.3 |
| Example 8 | 38,581 | 437,513 | 4,166 | 3.8 |
| Example 9 | 46,916 | 384,151 | 3,305 | 0.5 |
| Example 10 | 52,262 | 487,796 | 4,109 | 0.4 |
| Example 11 | 42,342 | 506,389 | 4,511 | 2.3 |

TABLE 2

Values from a calculation unit using the values of Table 1

| | PMMA ratio | PS ratio | Homopolymer ratio | CD estimation (nm) |
|---|---|---|---|---|
| Example 1 | 35 | 65 | 0.05 | 29.6 |
| Example 2 | 36 | 64 | 0.12 | 31.8 |
| Example 3 | 28 | 72 | 1.60 | 56.3 |
| Example 4 | 13 | 87 | 16.44 | 62.9 |
| Example 5 | 28 | 72 | 6.88 | 45.4 |
| Example 6 | 22 | 78 | 5.22 | 35.1 |
| Example 7 | 34 | 66 | 0.20 | 35.8 |
| Example 8 | 47 | 53 | 2.01 | 24.5 |
| Example 9 | 55 | 45 | 0.23 | 27.5 |
| Example 10 | 57 | 43 | 0.18 | 29.6 |
| Example 11 | 53 | 47 | 1.11 | 25.9 |

According to example embodiments, three factors including BCP molecular weight, block ratio in a BCP, and homopolymer ratio may be measured precisely by removing or deducting interference of a homopolymer. A critical dimension of patterns formed by a DSA method may be predicted or determined utilizing the measured factors, and a desired target pattern may be formed. The evaluation system of BCP patterns may be widely implemented for forming a fine contact or a fine contact hole in a volatile memory device, e.g., a DRAM device, a non-volatile memory device such as a flash device, or a logic device through the DSA method.

The methods, processes, and/or operations described herein may be performed by code or instructions to be executed by a computer, processor, controller, or other signal processing device. The computer, processor, controller, or other signal processing device may be those described herein or one in addition to the elements described herein. Because the algorithms that form the basis of the methods (or operations of the computer, processor, controller, or other signal processing device) are described in detail, the code or instructions for implementing the operations of the method embodiments may transform the computer, processor, controller, or other signal processing device into a special-purpose processor for performing the methods herein.

The analyzing, interference removing, calculation, determining, and other units and processing features of the embodiments described herein may be implemented in logic which, for example, may include hardware, software, or both. When implemented at least partially in hardware, the analyzing, interference removing, calculation, determining, and other units and processing features may be, for example, any one of a variety of integrated circuits including but not limited to an application-specific integrated circuit, a field-programmable gate array, a combination of logic gates, a system-on-chip, a microprocessor, or another type of processing or control circuit.

When implemented in at least partially in software, the analyzing, interference removing, calculation, determining, and other units and processing features may include, for example, a memory or other storage device for storing code or instructions to be executed, for example, by a computer, processor, microprocessor, controller, or other signal processing device. The computer, processor, microprocessor, controller, or other signal processing device may be those described herein or one in addition to the elements described herein. Because the algorithms that form the basis of the methods (or operations of the computer, processor, microprocessor, controller, or other signal processing device) are described in detail, the code or instructions for implementing the operations of the method embodiments may transform the computer, processor, controller, or other signal processing device into a special-purpose processor for performing the methods described herein.

Example embodiments have been disclosed herein, and although specific terms are employed, they are used and are to be interpreted in a generic and descriptive sense only and not for purpose of limitation. In some instances, as would be apparent to one of skill in the art as of the filing of the present application, features, characteristics, and/or elements described in connection with a particular embodiment may be used singly or in combination with features, characteristics, and/or elements described in connection with other embodiments unless otherwise indicated. Accordingly, it will be understood by those of skill in the art that various changes in form and details may be made without departing from the spirit and scope of the embodiments set forth in the claims.

What is claimed is:

1. An evaluation system of block copolymer patterns, comprising:
    a sample supplier providing a sample including a block copolymer and a homopolymer, the block copolymer including a first block and a second block;
    a molecular weight analyzer measuring a molecular weight of the block copolymer in the sample;
    a preliminary block ratio analyzer measuring a preliminary block ratio, the preliminary block ratio corresponding to a total ratio of the first and second blocks of the block copolymer in the sample;
    a homopolymer analyzer measuring a ratio of the homopolymer in the sample;

a homopolymer interference remover subtracting the ratio of the homopolymer from the preliminary block ratio and calculating a pure block ratio of each of the first and second blocks in the block copolymer;

a factor calculator generating pattern determining factors of the block copolymer; and a block critical dimension (CD) determiner estimating a block CD formed from the block copolymer, wherein the pattern determining factors include the molecular weight of the block copolymer, the ratio of the homopolymer in the sample and the pure block ratio of each of the first and second blocks in the block copolymer, wherein the block CD is calculated based on the pattern determining factors, and wherein each of the molecular weight analyzer and the preliminary block ratio analyzer includes a gel permeation chromatography (GPC) device.

2. The evaluation system as claimed in claim 1, wherein the molecular weight analyzer and the preliminary block ratio analyzer are integrated into a same device, and the integrated device measures each of the molecular weight of the block copolymer and the preliminary block ratio of the first and second blocks of the block copolymer in the sample.

3. The evaluation system as claimed in claim 2, wherein a single GPC device serves as the molecular weight analyzer and the preliminary block ratio analyzer.

4. The evaluation system as claimed in claim 3, further comprising:

at least two different detectors coupled to the GPC device.

5. The evaluation system as claimed in claim 4, wherein the detectors include a refractive index detector (RID) and an ultraviolet detector (UVD).

6. The evaluation system as claimed in claim 1, wherein the homopolymer analyzer includes a high-performance liquid chromatography (HPLC) device.

7. The evaluation system as claimed in claim 1, wherein:

the molecular weight analyzer and the preliminary block ratio analyzer are integrated into one molecular weight/preliminary block ratio analyzer, and the homopolymer analyzer and the molecular weight/preliminary block ratio analyzer are sequentially and serially connected.

8. The evaluation system as claimed in claim 7, wherein:

the homopolymer analyzer includes an HPLC device, and the molecular weight/preliminary block ratio analyzer includes a single GPC device serially connected to the HPLC device.

9. The evaluation system as claimed in claim 7, further comprising:

a mixer between the homopolymer analyzer and the molecular weight/preliminary block ratio analyzer, wherein polymers are to be recollected in the mixer.

* * * * *